United States Patent
Varlet et al.

(10) Patent No.: US 11,549,958 B2
(45) Date of Patent: Jan. 10, 2023

(54) INTELLIGENT HANDLING OF MATERIALS

(71) Applicant: Beckman Coulter, Inc., Brea, CA (US)

(72) Inventors: Eric Varlet, Ronchin (FR); Sohrab Faramarzi Oghani, Villeneuve d'Ascq (FR); Martin Bué, Lille (FR); Pr. El Ghazali Talbi, Lille (FR)

(73) Assignee: Beckman Coulter, Inc., Brea, CA (US)

( * ) Notice: Subject to any disclaimer, the term of this patent is extended or adjusted under 35 U.S.C. 154(b) by 604 days.

(21) Appl. No.: 16/468,430

(22) PCT Filed: Dec. 8, 2017

(86) PCT No.: PCT/US2017/065345
§ 371 (c)(1),
(2) Date: Jun. 11, 2019

(87) PCT Pub. No.: WO2018/111721
PCT Pub. Date: Jun. 21, 2018

(65) Prior Publication Data
US 2021/0072268 A1 Mar. 11, 2021

Related U.S. Application Data

(60) Provisional application No. 62/432,930, filed on Dec. 12, 2016.

(51) Int. Cl.
*G01N 35/00* (2006.01)
*G16H 40/67* (2018.01)
(Continued)

(52) U.S. Cl.
CPC ......... *G01N 35/0092* (2013.01); *G16H 10/40* (2018.01); *G16H 40/67* (2018.01);
(Continued)

(58) Field of Classification Search
CPC ....... G01N 35/0092; G01N 2035/0094; G01N 2035/1032; G01N 2035/00881;
(Continued)

(56) References Cited

U.S. PATENT DOCUMENTS 6,581,012 B1 * 6/2003 Aryev .............. G05B 19/41865
702/22
6,594,588 B1 * 7/2003 Peden ....................... G06F 8/34
707/999.106
(Continued)

FOREIGN PATENT DOCUMENTS

| CN | 101065742 | 10/2007 |
|---|---|---|
| CN | 102759630 | 8/2016 |

(Continued)

OTHER PUBLICATIONS

International Search Report and Written Opinion dated Apr. 25, 2018 for Application No. PCT/US2017/065345, 13 pgs.

(Continued)

*Primary Examiner* — Shogo Sasaki
(74) *Attorney, Agent, or Firm* — Frost Brown Todd LLC (57) ABSTRACT

In a scenario where a laboratory is required to perform a plurality of tests on biological samples from a plurality of tubes in a manner that satisfies certain constraints, it is possible that the laboratory could handle the samples and assign them to machines in a manner which ensures that the relevant constraints are met. This could include using matrices and optimization functions to represent tubes, tests, machines and prescriptions, and could also include dynamically determining whether and how to aliquot the samples so as to meet the constraints given the conditions under which the samples would be processed.

11 Claims, 10 Drawing Sheets (51) Int. Cl.
*G16H 10/40* (2018.01)
*G01N 35/10* (2006.01)

(52) U.S. Cl.
CPC ............. *G01N 2035/0094* (2013.01); *G01N 2035/1032* (2013.01)

(58) Field of Classification Search
CPC ......... G01N 35/00871; G01N 35/1016; G01N 35/00722; G01N 35/0095; G01N 2035/009; B01L 2200/14; B01L 3/021; G16H 50/70; G16H 10/40; G16H 40/67
See application file for complete search history.

(56) References Cited

U.S. PATENT DOCUMENTS

| | | | |
|---|---|---|---|
| 8,112,229 B2 | 2/2012 | Fritchie et al. | |
| 2002/0147515 A1* | 10/2002 | Fava | G05B 19/41865 700/95 |
| 2005/0037502 A1* | 2/2005 | Miller | G01N 35/00 436/43 |
| 2007/0196909 A1* | 8/2007 | Showalter | G06Q 10/06 435/283.1 |
| 2007/0282476 A1* | 12/2007 | Song | G16H 40/20 705/7.18 |
| 2008/0235055 A1* | 9/2008 | Mattingly | G16H 10/40 705/2 |
| 2008/0300789 A1* | 12/2008 | Fritchie | G01N 35/0092 702/1 |
| 2012/0109531 A1* | 5/2012 | Knafel | G05B 19/41865 702/19 |
| 2018/0340949 A1* | 11/2018 | Maetzler | G01N 35/1016 |

FOREIGN PATENT DOCUMENTS

| | | |
|---|---|---|
| EP | 2 821 795 A1 | 1/2015 |
| JP | 2003-315348 A | 11/2003 |
| WO | WO 2015/126839 A1 | 8/2015 |

OTHER PUBLICATIONS

Chinese Office Action dated Sep. 21, 2022 for Application No. 201780083174.0, 13 pages.

* cited by examiner

Tube-Test Matrix

- This matrix indicates the required tests to be done on each tube type.
- ✓ This matrix is changed by aliquoting.

Machine-Test Matrix

- This matrix shows the capability of the existing machines in the core lab. It presents the tests that each machine can do.

Impact of Aliquoting on Tube-Machine Matrix

Initial Tube-Machine Matrix

| | | M I | M II | M III | M IV |
|---|---|---|---|---|---|
| 90 | T 1 | + | - | - | - |
| 70 | T 2 | - | + | - | - |
| 160 | T 3 | - | - | + | - |
| 47 | T 4 | - | - | - | + |
| 130 | T 5 | + | + | - | - |
| 280 | T 6 | + | - | + | - |
| 402 | T 7 | + | - | - | + |
| 85 | T 8 | - | + | + | - |
| 310 | T 9 | - | + | - | + |
| 0 | T 10 | - | - | + | + |
| 78 | T 11 | + | + | + | - |
| 208 | T 12 | + | + | - | + |
| 0 | T 13 | + | - | + | + |
| 300 | T 14 | - | + | + | + |
| 40 | T 15 | + | + | + | + |

$\sum = 2200$

Assume it takes a lot of time to send one tube to the all four machines

Tubes which need all machines cannot pass TAT constraint

Final Tube-Machine Matrix

| | | M I | M II | M III | M IV |
|---|---|---|---|---|---|
| 130 (40) | T 1 | + | - | - | - |
| 70 | T 2 | - | + | - | - |
| 160 | T 3 | - | - | + | - |
| 47 | T 4 | - | - | - | + |
| 130 | T 5 | + | + | - | - |
| 280 | T 6 | + | - | + | - |
| 402 | T 7 | + | - | - | + |
| 85 | T 8 | - | + | + | - |
| 310 | T 9 | - | + | - | + |
| 0 | T 10 | - | - | + | + |
| 78 | T 11 | + | + | + | - |
| 208 | T 12 | + | + | - | + |
| 0 | T 13 | + | - | + | + |
| 340 (40) | T 14 | - | + | + | + |
| 0 | T 15 | + | + | + | + |

$\sum = 2240$

FIG. 12

Impact of Aliquoting on Tube-Machine Matrix

Initial Tube-Machine Matrix

| | | M I | M II | M III | M IV |
|---|---|---|---|---|---|
| 90 | T 1 | + | - | - | - |
| 70 | T 2 | - | + | - | - |
| 160 | T 3 | - | - | + | - |
| 47 | T 4 | - | - | - | + |
| 130 | T 5 | + | + | - | - |
| 280 | T 6 | + | - | + | - |
| 402 | T 7 | + | - | - | + |
| 85 | T 8 | - | + | + | - |
| 310 | T 9 | - | + | - | + |
| 0 | T 10 | - | - | + | + |
| 78 | T 11 | + | + | + | - |
| 208 | T 12 | + | + | - | + |
| 0 | T 13 | + | - | + | + |
| 300 | T 14 | - | + | + | + |
| 40 | T 15 | + | + | + | + |

$\sum = 2200$

Assume M I is far from other machines

TAT constraint for tubes which need M I and other machines is not met

Final Tube-Machine Matrix

| | | M I | M II | M III | M IV |
|---|---|---|---|---|---|
| 1228 (1138) | T 1 | + | - | - | - |
| 200 (130) | T 2 | - | + | - | - |
| 440 (280) | T 3 | - | - | + | - |
| 449 (402) | T 4 | - | - | - | + |
| 0 | T 5 | + | + | - | - |
| 0 | T 6 | + | - | + | - |
| 0 | T 7 | + | - | - | + |
| 163 (78) | T 8 | - | + | + | - |
| 518 (208) | T 9 | - | + | - | + |
| 0 | T 10 | - | - | + | + |
| 0 | T 11 | + | + | + | - |
| 0 | T 12 | + | + | - | + |
| 0 | T 13 | + | - | + | + |
| 340 (40) | T 14 | - | + | + | + |
| 0 | T 15 | + | + | + | + |

$\sum = 3338$

Impact of Aliquoting on Tube-Machine Matrix

Initial Tube-Machine Matrix

|     |      | M I | M II | M III | M IV |
|-----|------|-----|------|-------|------|
| 90  | T 1  | +   | -    | -     | -    |
| 70  | T 2  | -   | +    | -     | -    |
| 160 | T 3  | -   | -    | +     | -    |
| 47  | T 4  | -   | -    | -     | +    |
| 130 | T 5  | +   | +    | -     | -    |
| 280 | T 6  | +   | -    | +     | -    |
| 402 | T 7  | +   | -    | -     | +    |
| 85  | T 8  | -   | +    | +     | -    |
| 310 | T 9  | -   | +    | -     | +    |
| 0   | T 10 | -   | -    | +     | +    |
| 78  | T 11 | +   | +    | +     | -    |
| 208 | T 12 | +   | +    | -     | +    |
| 0   | T 13 | +   | -    | +     | +    |
| 300 | T 14 | -   | +    | +     | +    |
| 40  | T 15 | +   | +    | +     | +    |

$\sum = 2200$

→ TAT constraint for tubes which need more than one machine is not met →

Final Tube-Machine Matrix

|             |      | M I | M II | M III | M IV |
|-------------|------|-----|------|-------|------|
| 1228 (1138) | T 1  | +   | -    | -     | -    |
| 1221 (1151) | T 2  | -   | +    | -     | -    |
| 943 (783)   | T 3  | -   | -    | +     | -    |
| 1307 (1260) | T 4  | -   | -    | -     | +    |
| 0           | T 5  | +   | +    | -     | -    |
| 0           | T 6  | +   | -    | +     | -    |
| 0           | T 7  | +   | -    | -     | +    |
| 0           | T 8  | -   | +    | +     | -    |
| 0           | T 9  | -   | +    | -     | +    |
| 0           | T 10 | -   | -    | +     | +    |
| 0           | T 11 | +   | +    | +     | -    |
| 0           | T 12 | +   | +    | -     | +    |
| 0           | T 13 | +   | -    | +     | +    |
| 0           | T 14 | -   | +    | +     | +    |
| 0           | T 15 | +   | +    | +     | +    |

$\sum = 4699$

INTELLIGENT HANDLING OF MATERIALS

This application is a National Stage Entry of PCT Application No. PCT/US17/65345, entitled "Intelligent Handling of Materials," filed Dec. 8, 2017, which claims priority to U.S. Provisional Application No. 62/432,930, entitled "Intelligent Handling of Biological Samples," filed Dec. 12, 2016, the disclosures of which are incorporated by reference herein.

TECHNICAL FIELD

This disclosure relates to an improved way of handling materials.

BACKGROUND

Generally, in the context of performing laboratory tests on human biological materials, a number of tubes drawn from a patient may vary according to a variety of factors. On one hand, there may be health benefits to removing as little sample material (e.g., blood) as possible from a patient. On the other hand, collecting multiple tubes of biological material may be beneficial in that it may allow for tests to be run on different instruments in parallel, thereby enabling results and associated medical treatments to be provided at the earliest possible instance. Various ways of balancing these competing considerations, such as using policies to determine how much material to collect from a patient, or separating samples into separate tubes after collecting the samples, have been tried, and known techniques suffer from one or more disadvantages in handling biological materials. Accordingly, there is a need for an improved technology for handling of biological material in order to ameliorate the known disadvantages in handling biological materials.

SUMMARY

Embodiments of the disclosed technology can be applied in a variety of manners. For example, based on the material disclosed herein, it is possible that one of ordinary skill in the art could implement a machine comprising a plurality of laboratory instruments, at least one aliquoter, and at least one system comprising a memory and a processor. In such an embodiment, each of the laboratory instruments from the plurality of laboratory instruments may be adapted to perform at least one test. Similarly, in some such embodiments, the system may be configured with instructions adapted to cause it to, when executed, perform steps comprising determining one or more ways to separate samples contained in a plurality of tubes into additional tubes, and separating, suing the at least one aliquoter, the samples contained in the plurality of tubes based on evaluating results corresponding to the one or more ways to separate the samples.

Further information on how the disclosed technology could potentially be implemented is set forth herein, and variations on the sample will be immediately apparent to and could be practiced without undue experimentation by those of ordinary skill in the art based on the material which is set forth in this document. Accordingly, the exemplary methods and machines described in this summary should be understood as being illustrative only, and should not be treated as limiting on the scope of protection provided by this or any related document.

DETAILED DESCRIPTION

Embodiments of the present disclosure may be used to address problems related to the appropriate handling of samples of biological materials for testing, and particularly addressing an issue of appropriately separating a single sample into multiple portions (i.e., aliquoting the samples) to address competing concerns such as reduction of turn-around time and maximization of usable material. In one aspect, the disclosed technology relates to techniques for aliquoting such biological samples in a manner which accounts for various conditions and requirements as they may exist when the samples are to be processed. In some embodiments, this may addresses competing objectives such as maximizing throughput and minimizing the number of tubes to be processed. For purpose of illustration, embodiments disclosed herein focuses on the application of the inventors' technology in that context. However, it should be understood that the technology disclosed herein could be used for other purposes and in other contexts as well. In an example embodiment, rather than being used in the context of handling biological material such as patient samples in a laboratory, the disclosed technology could be applied in the context of handling materials of non-biological origin as well, such as chemical samples which may be tested for the presence of various unexpected materials (e.g., contaminants). Accordingly, embodiments disclosed herein should be understood as being provided only by way of illustrative example, and numerous modifications and alternate embodiments of the disclosure may occur to those skilled in the art.

Embodiments of the present disclosure could be applied in a variety of manners. For example, based on the disclosure set forth herein, one of ordinary skill in the art could implement a machine comprising a plurality of laboratory instruments adapted to perform one or more types of test, an aliquoter, and a computer configured with instructions adapted to cause it (when executed) to perform an aliquot definition process. Such an aliquot definition process could comprise determining one or more ways of separating samples of biological material contained in a plurality of tubes into additional tubes, determining results corresponding to those ways of separating the samples of biological material contained in the plurality of tubes into additional tubes, and approving one of the ways of separating the samples of biological material contained in the plurality of tubes into additional tubes based on evaluating the one or more results. In such a case, the determination of the one or more ways of separating the samples of biological material contained in the plurality of tubes into additional tubes could be based on factors such as a first matrix indicating a plurality of tests to be performed on the samples of biological material, and a second matrix indicating types of test which the laboratory instruments are adapted to perform.

As another example, based on the material disclosed herein, it is possible that one of ordinary skill in the art could implement a method comprising steps such as determining a potential way of separating samples contained in a plurality of tubes into additional tubes, determining whether to approve the potential way of separating the samples contained in the plurality of tubes into additional tubes, and repeating those steps until a determined way to separate the samples contained in the plurality of tubes is approved.

In some embodiments, a method such as described in the preceding paragraph may be implemented such that, each time the determining steps are repeated, the potential way of separating samples contained in the plurality of tubes into additional tubes separates the samples into more additional tubes than a most recent previously determined way of separating the samples.

In some embodiments, a method such as described in either of the preceding two paragraphs may comprise determining an initial way of separating the samples contained in the plurality of tubes into additional tubes; determining an initial result corresponding to the initial way of separating the samples contained in the plurality of tubes into additional tubes; determining whether to approve the initial way of separating the samples contained in the plurality of tubes into additional tubes based on evaluating the initial result, and until a way of separating the samples contained in the plurality of tubes into additional tubes is approved repeating a set of steps. These steps may include determining a new way of separating the samples contained in the plurality of tubes into additional tubes wherein the new way increases how many additional tubes the samples are separated into relative to a most recent previously determined way of separating the samples, determining a new result corresponding to the new way of separating the samples, and determining whether to approve the new way of separating the samples based on evaluating the new result.

In some embodiments, a method such as described in the previous paragraph could be implemented such that the initial way of separating the samples contained in the plurality of tubes is not separating the samples contained in the plurality of tubes into additional tubes.

In some embodiments, a method such as described in any of the preceding four paragraphs could be implemented such that determining ways of separating samples contained the plurality of tubes and determining one or more results of such separation are performed in parallel for each of a plurality of aliquoting (i.e., separating a single sample into multiple portions) policies.

In some embodiments, a method such as described in any of the preceding five paragraphs could be implemented to include evaluating results of separating samples in a manner which comprises determining the impact of the results on at least one key performance indicator.

In some embodiments, a method such as described in any of the preceding six paragraphs could be implemented to include evaluating results of separating samples which comprises determining whether each of the evaluated results corresponds to satisfying a requirement for processing the samples, and to include approving a way of separating the samples even when none of the evaluated results corresponds to satisfying the requirement for processing the samples.

In some embodiments, a method such as described in any of the preceding seven paragraphs could be implemented to determine ways of separating samples based on a first matrix indicating tests to be performed on the samples and a second matrix indicating types of tests which laboratory instruments are adapted to perform.

In some embodiments, a method such as described in any of the preceding eight paragraphs could be implemented to perform the determining and approval steps described previously using a virtual machine hosted in a remote computing facility which is remote from an aliquoter and a plurality of laboratory instruments.

Machine and computer program product embodiments are also possible. For example, some embodiments could comprise machines adapted to perform the methods described in any of the preceding paragraphs. Similarly, some embodiments could comprise computer program products comprising computer readable media encoding instructions for performing methods described in any of the preceding paragraphs.

In other embodiments, there may be a machine comprising a plurality of laboratory instruments, at least one aliquoter, and a computer. In such an embodiment, each of the laboratory instruments may be adapted to perform one or more types of test. Additionally, in such an embodiment, the computer may be configured with instructions adapted to cause it to, when executed, perform an aliquot definition process. Such an aliquot definition process may comprise determining one or more ways of using the at least one aliquoter to separate samples contained in a plurality of tubes into additional tubes, and approving one of the one or more ways of using the at least one aliquoter to separate samples based on evaluating results corresponding to the one or more ways of using the at least one aliquoter to separate the samples.

Figure 1:
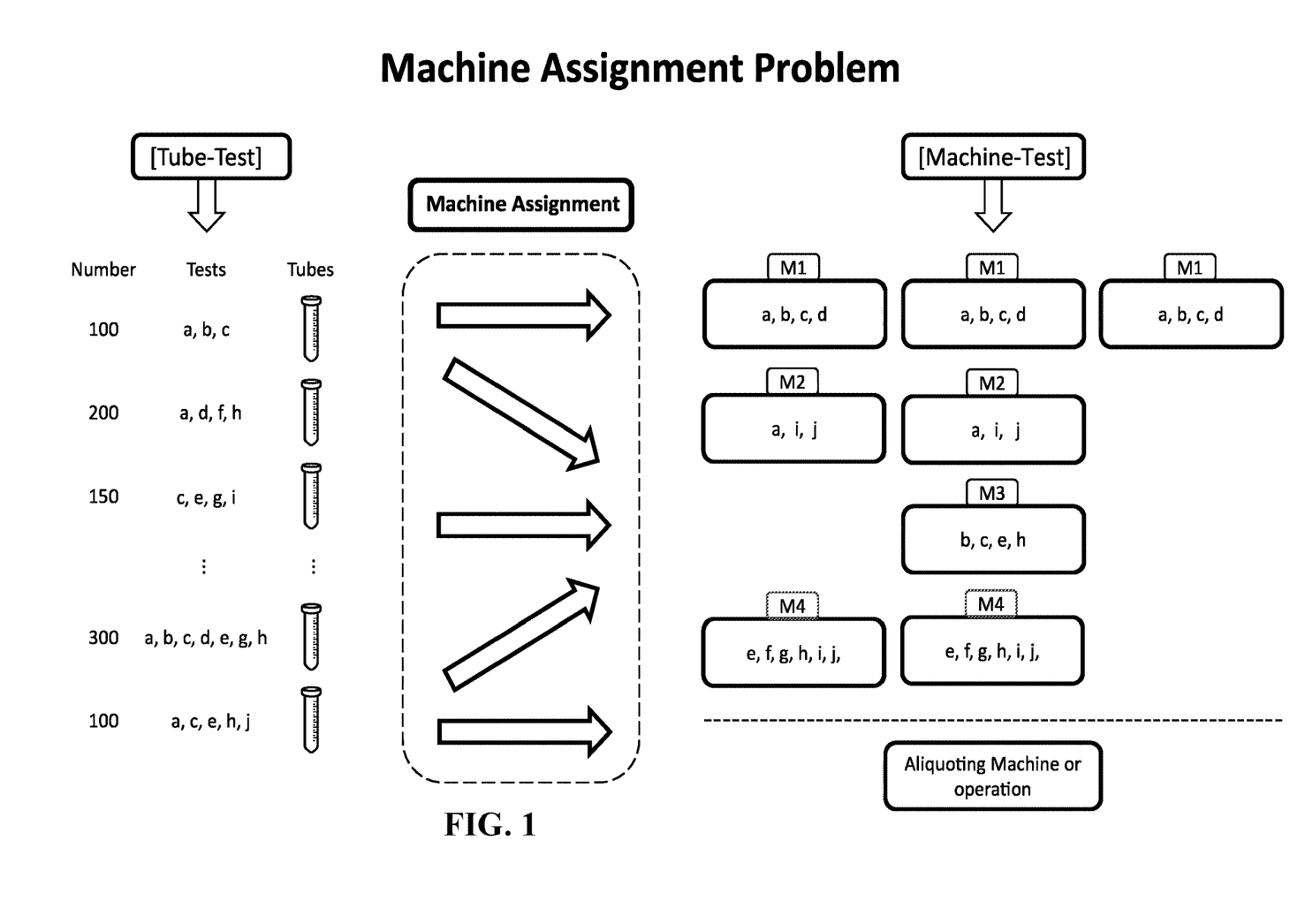
FIG. 1 illustrates an exemplary embodiment of a basic problem faced by a laboratory in determining which tests to perform on which tubes using which of the lab's machines.

Turning now to the Figures, FIG. 1 is an exemplary embodiment of a diagram illustrating a basic problem faced by a laboratory. Determining which tests will be performed on which tubes by which of the lab's machines is a challenge. In the scenario illustrated in FIG. 1, a lab has received tubes from various sources (e.g., hospitals, doctor's offices, etc.), which need to have various tests performed on them. In an example embodiment, a lab may receive 100 tubes whose contents needed to be subjected to tests a, b, and c; 200 tubes whose contents needed to be subjected to tests a, d, f, and h; 150 tubes whose contents needed to be subjected to tests c, e, g, and i; etc. As shown on the right side of FIG. 1, the lab may also have multiple machines which could be used to perform the necessary tests. In an example embodiment, the lab may have three machines of type M1, which are capable of doing tests a, b, c, and d; two machines of type M2, which are capable of doing tests a, i, and j; etc. The problem, then, is to determine how the various tubes should be allocated to and routed between the various available machines so that the necessary tests could be completed faster and in an easy way.

Figure 2:
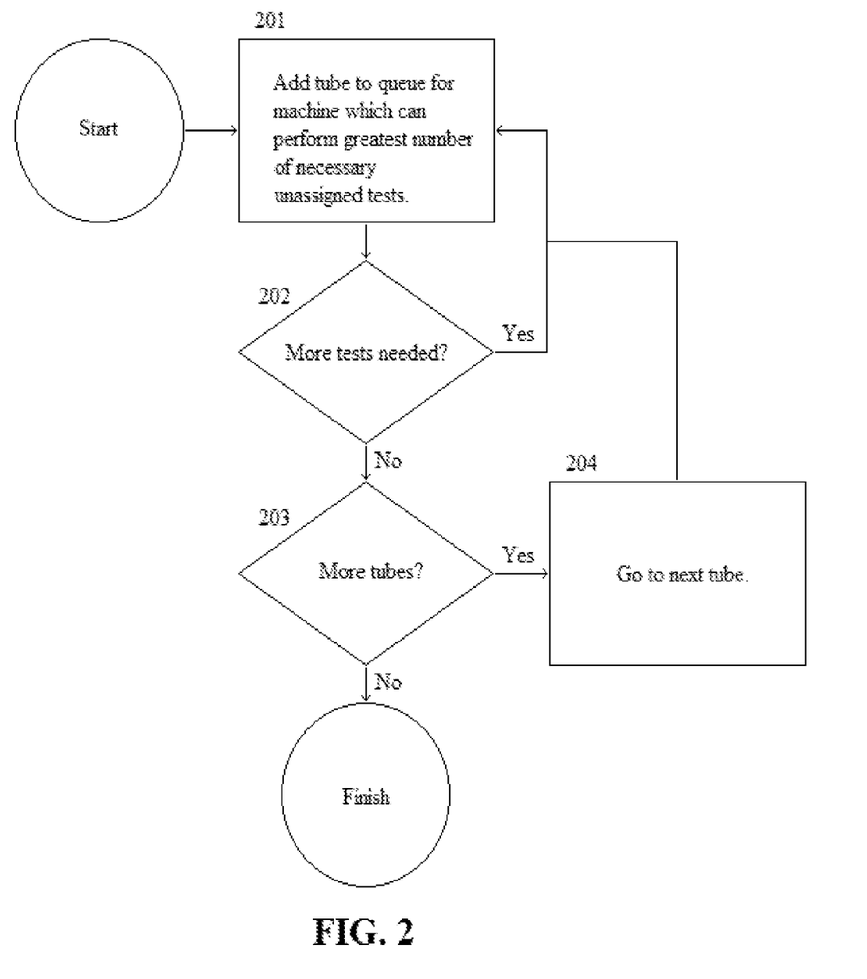
FIG. 2 illustrates an exemplary embodiment of a procedure used to allocate tubes among machines.

In one embodiment, a variety of approaches may be used to address such problems. In an example embodiment, it may be possible that tubes are allocated using a procedure such as illustrated in FIG. 2. In a further embodiment, the procedure would begin by taking a first unallocated tube and adding it to a queue for a machine that could perform the greatest number of tests for that tube 201. In an example embodiment in the situation illustrated in FIG. 1, the step may be performed by taking one of the hundred tubes with contents upon which tests a, b, and c need to be performed, and adding it to a queue for one of the machines of type M1, since those machines may be capable of performing all of the tests for those tubes. In a further embodiment, after the tube had been added to a queue 201, a check may be made of whether more tests may be necessary 202. In a further embodiment, if there were more tests necessary (e.g., because the tube had been added to the queue for a machine which wasn't able to perform all of the necessary tests), then the process may be repeated, with the tube being added to a queue 201 for another machine which was capable of performing one or more of the tests which wouldn't be taken care of by the machines for which the tube had already been enqueued (i.e., into whose queues the tube had already been assigned). In an alternate embodiment, if no more tests are needed to be performed, then a check may be made to determine if there were more tubes which had not been allocated to machines 203. In a further embodiment, if there were more tubes, then the process could iterate 204 to the next tube (e.g., the second tube from the set of the hundred tubes with contents that needed to be subjected to tests a, b and c) and add that tube to a queue 201 as appropriate. Otherwise, the allocation of tubes to machines could be deemed to be finished, and the physical tubes could be routed between the machines and tested in a manner corresponding to their queue assignments.

While an algorithm such as shown in FIG. 2 could be used to allocate tubes to machines, such an algorithm could have significant drawbacks. For example, if (as described above) tubes requiring tests a, b, and c were allocated to the machines of type M1, then the machines of type M1 could unnecessarily become a bottleneck, since any tube which needed test d would have to be processed by a machine of type M1, while a tube which needed only tests a, b and c could potentially be processed using a machine of type M1, or a machine of type M2 (to perform test a) in combination with a machine of type M3 (to perform tests b and c).

Figure 3:
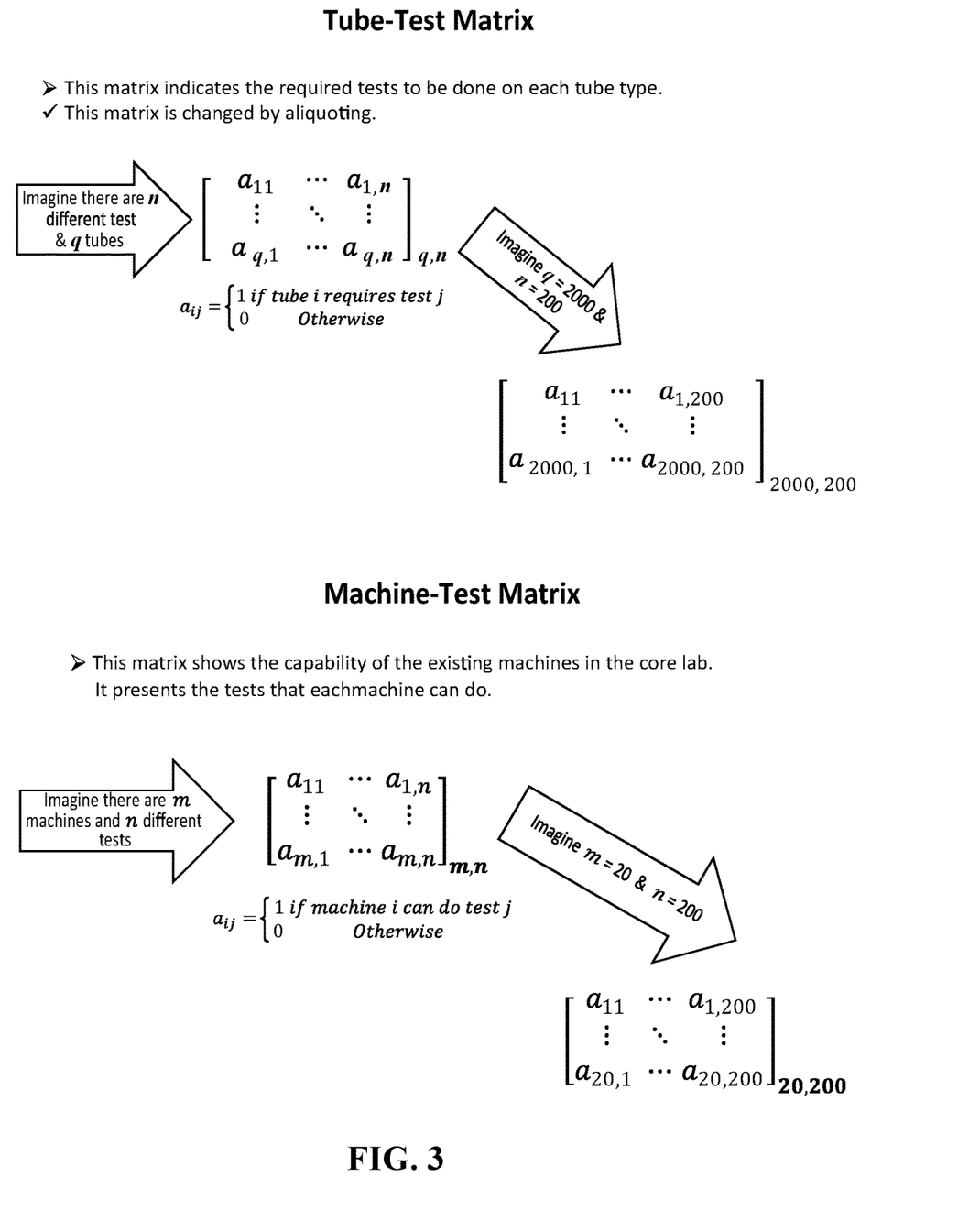
FIG. 3 illustrates an exemplary embodiment of matrices which may be used to store information about tests required for particular tubes and tests performed by machines.
Figure 4:
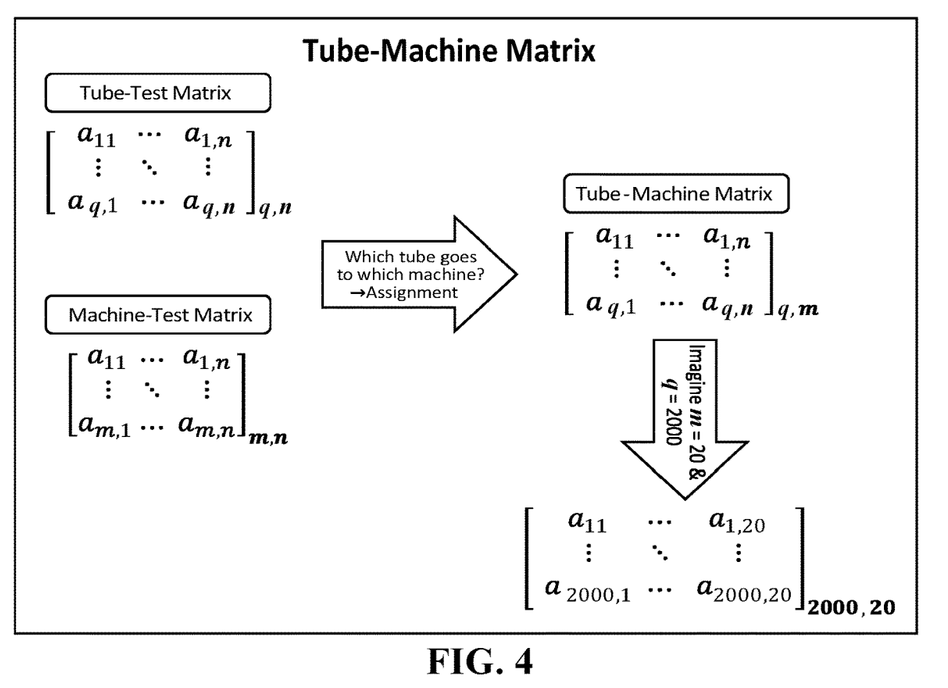
FIG. 4 illustrates an exemplary embodiment of a matrix used to represent how tubes should be allocated to machines within a lab.

Accordingly, for this and other reasons, rather than using a naïve assignment process such as shown in FIG. 2, tubes will preferably be assigned to machines in a more sophisticated manner For example, in some embodiments, matrices such as shown in FIG. 3 (Tube-Test Matrix and Machine-Test Matrix) may be used to store information about which tests are required for which tube, and which machines can perform those tests. These matrices may then be used as input to an optimization function (e.g., the Hungarian algorithm, the auction algorithm, or other algorithm used to solve the assignment problem) to create a matrix such as shown in FIG. 4 (Tube-Machine Matrix) which indicates how the tubes should be allocated to the various machines in the lab. Other matrix representations are also possible. For example, while FIG. 3 illustrated a Tube-Test Matrix as having one row for each possible combination of tests, in some embodiments it is possible that instead a Tube-Test Matrix may have one row for each tube, so that instead of having $2^n-1$ rows where n is the number of tests, a Tube-Test Matrix may have q rows, where q is the number of tubes. Accordingly, the Tube-Test, Machine-Test, and Tube-Machine matrices illustrated in FIGS. 3-4 should be understood as being illustrative only, and should not be treated as limiting.

Figure 5:
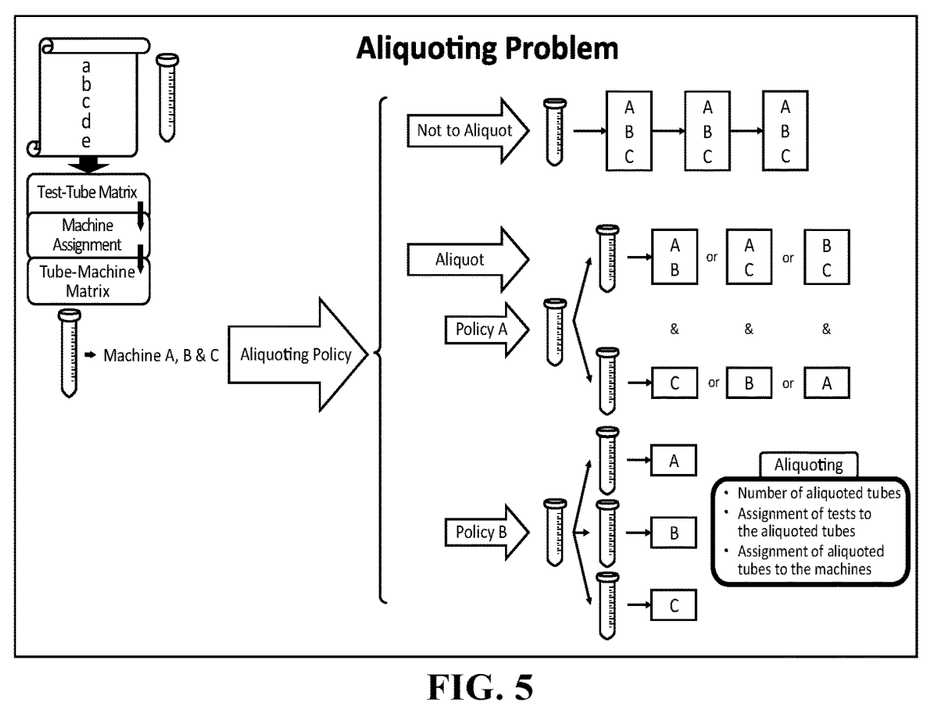
FIG. 5 illustrates an exemplary embodiment of how aliquoting can be used to permit parallel operation on material from a single tube.

However, even a more sophisticated matrix based optimization approach such as described above may not be sufficient in all cases. To illustrate, consider the simplified case of a single tube with contents that need to be subjected to tests on three different machines. If turnaround time is not a concern, then this can be achieved simply by assigning the tube to the first machine (machine A), followed by the second machine (machine B), followed by the third machine (machine C). However, it is possible that there may be a turnaround time constraint that may make this impractical, such as if each of the relevant machines (i.e., machines A, B and C) had a turnaround time of one hour, but the tube was from a hospital whose contract with the laboratory doing the tests required testing on tubes be completed within 150 minutes of the tube's arrival (i.e., turnaround time of two and a half hours). To address this, in some embodiments the laboratory may aliquot the tube—that is separate the contents of the tube into multiple tubes. In this way, in some embodiments, tests may be run on two or more of the relevant machines in parallel, thereby making it possible for the 150 minute turnaround time requirement to be met even though each of the machines would require 60 minutes to complete its test(s). A diagram illustrating how aliquoting may be used in some embodiments to permit parallel operation on material from a single tube is presented in FIG. 5. A diagram illustrating how aliquoting may be integrated in some embodiments into a matrix based optimization workflow such as described above is illustrated in FIG. 6, in which tubes would be aliquoted according to a predefined aliquoting policy, and the Tube-Test Matrix would be used to reflect the tubes as aliquoted, rather than the tubes as originally provided.

Figure 6:
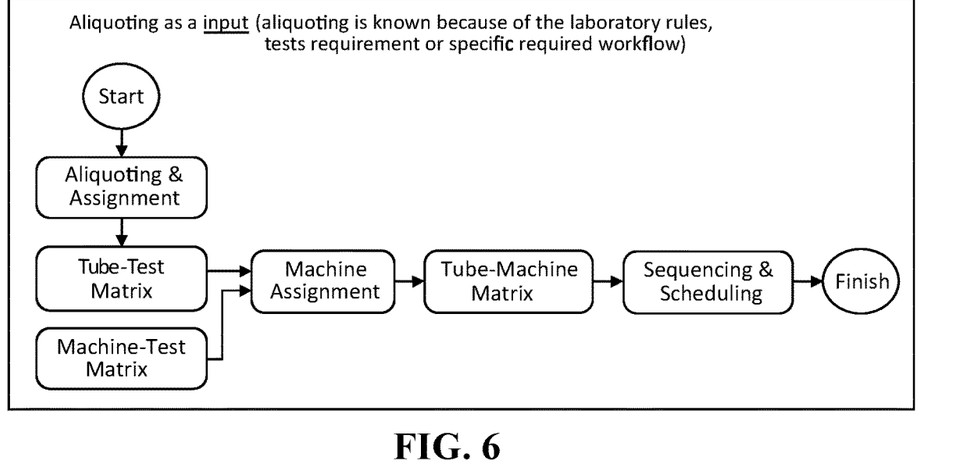
FIG. 6 illustrates an exemplary embodiment of how aliquoting can be integrated into a matrix based optimization workflow.
Figure 8:
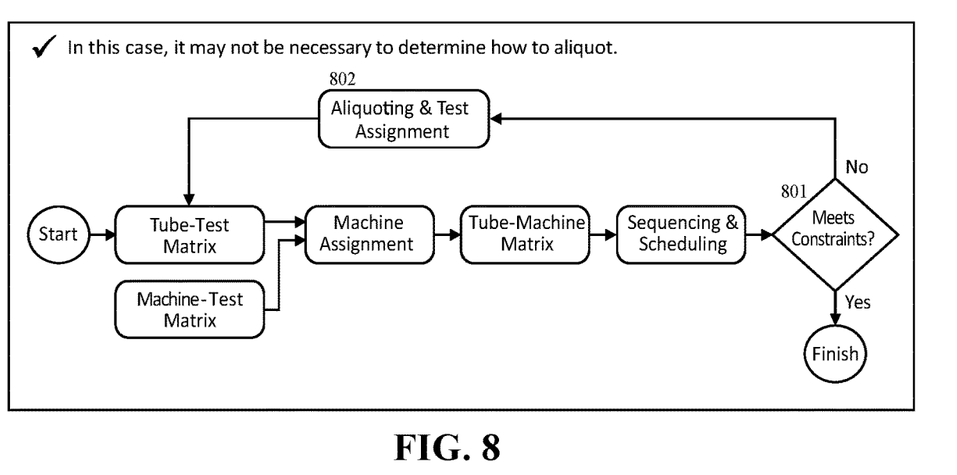
FIG. 8 illustrates an exemplary embodiment of a workflow in which aliquoting is determined dynamically.

While aliquoting of tubes can potentially decrease turnaround time by enabling the contents of a single tube to be tested by multiple machines in parallel, there are drawbacks that should be considered as well. For example, an aliquoting machine can itself become a bottleneck, potentially leading to increased turnaround times if aliquoting is performed indiscriminately. Additionally, due to dead volumes in tubes, aliquoting can have the result of decreasing the effective amount of a sample which is available for testing. Accordingly, in some embodiments, rather than simply aliquoting tubes based on a fixed policy in a manner such as shown in FIG. 6, preferably aliquoting of tubes (including whether a tube should be aliquoted at all) may be determined dynamically, using an alternative workflow such as shown in FIGS. 8, 15, 16 and 17. In the workflow of FIG. 8, rather than simply aliquoting according to a fixed policy, or distributing tubes to machines once a Tube-Machine Matrix has been created, after a Tube-Machine Matrix has been created and a sequence and schedule for distributing tubes to machines based on that matrix has been determined, a check 801 will be performed for whether distributing the tubes in that manner would satisfy various constraints place upon the lab. This could be done, for example, using a process such as shown in FIG. 9, discussed below.

Figure 9:
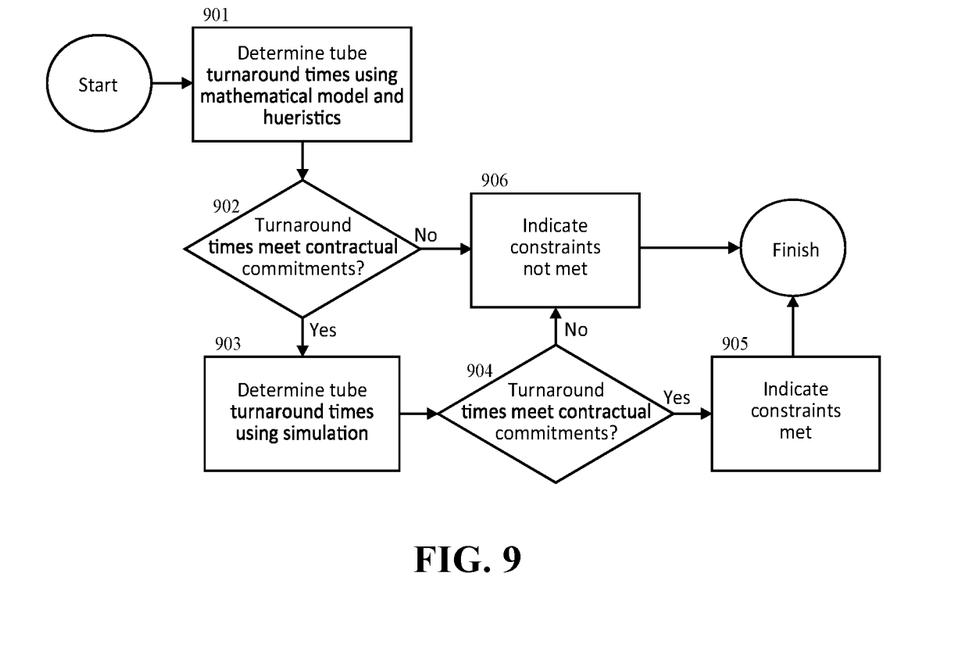
FIG. 9 illustrates an exemplary embodiment of a process for determining if constraints on a lab are met if tubes are distributed to machines in a particular manner.

In the process of FIG. 9, a mathematical model and heuristics would initially be used to determine the turnaround time for the tubes 901 (e.g., the time necessary for each tube to have the necessary tests performed on its contents could be determined based on the time each of the machines that tube was assigned to would need to perform its testing if operating in isolation under ideal conditions, and based on the assumption that the shortest processing time first heuristic would be used in ordering the tubes to be processed). The turnaround times for the tubes could then be checked 902 to confirm that they meet the labs' contractual commitments. If the check 902 indicated that the contractual commitments were met, then turnaround times could be re-determined using a simulation, which could differ from the previous determination 101 based on the use of information about the actual conditions in the lab. In some embodiments, such a simulation may consider factors such as:

current lengths of queues on the instruments and associated delays to complete the tests given the tubes in the queues;
  if the estimated future workload for the lab was such that a machine was likely to become a bottleneck when a new batch of tubes is added to the current queues;
  the time necessary to convey tubes between machines given the physical layout of the lab;
  the reagents on board the instruments and the corresponding tests that the machines could perform with those reagents; and/or
  effect of scheduled maintenance (e.g., reagent refill, calibration and control) on machine availability.

The check for whether the contractual turnaround time comments were met could then be repeated 904, and the process could indicate that the constraints either were 905 or were not 906 met based on that check.

Of course, in some embodiments, the check 801 for whether constraints are met in a workflow such as shown in FIG. 8 may be performed in ways other than via the process of FIG. 9. For example, while the process of FIG. 9 had separate steps for using mathematical models and simulations to determine turnaround time, in some embodiments it is possible that one of those steps could be omitted, and the check 801 of whether constraints are met may be performed using either only a simulation or only a mathematical model. Similarly, in some embodiments, it is possible that factors other than contractually mandated turnaround times could be considered when determining 801 whether constraints are met. For example, in some embodiments, the checks 902 904 shown in FIG. 9 may consider whether whatever level of aliquoting was being proposed would result in the usable amount of a tube's sample material falling below a threshold necessary for the tests (e.g., because of the dead volume in the tubes the sample is aliquoted into), either instead of, or in addition to, considering contractual turnaround time commitments. Further, in some embodiments, it is possible that a process such as shown in FIG. 9 may be skipped or rendered optional, such as by using a heuristic to determine if aliquoting could potentially make sense (e.g., treating aliquoting as pointless in a case where a deadline associated with a batch of tubes had already expired or in a case where aliquoting would increase the amount of sample lost to dead volume to the extent that it would prevent the necessary tests from being performed), and only proceeding with a process such as shown in FIG. 9 if the heuristic indicated that aliquoting had at least some potential benefit.

Additionally, even in embodiments where the general process of FIG. 9 is followed, variations may still be possible. For example, in some embodiments, the output of a process of FIG. 9 may be a simple YES/NO indication of whether the constraints were met. In other embodiments, the output of a process such as shown in FIG. 9 may include more information, such as which tubes a constraint was violated for, and the nature of the violation (e.g., an indication that the turnaround time for a particular tube was too long, because a particular machine that tube was assigned to was likely to become a bottleneck, because that tube had a short turnaround time yet was placed behind another tube in the queue for a machine, or because that machine was located far from the other machines in the lab and so using it would require considering the time to physically transport a tube to the machine). Accordingly, the discussion above of the process of FIG. 9, as well as the exemplary variations on that Figure, should be understood as being illustrative only, and should not be treated as being limiting on the scope of protection provided by this document or any other related document.

Figure 11:
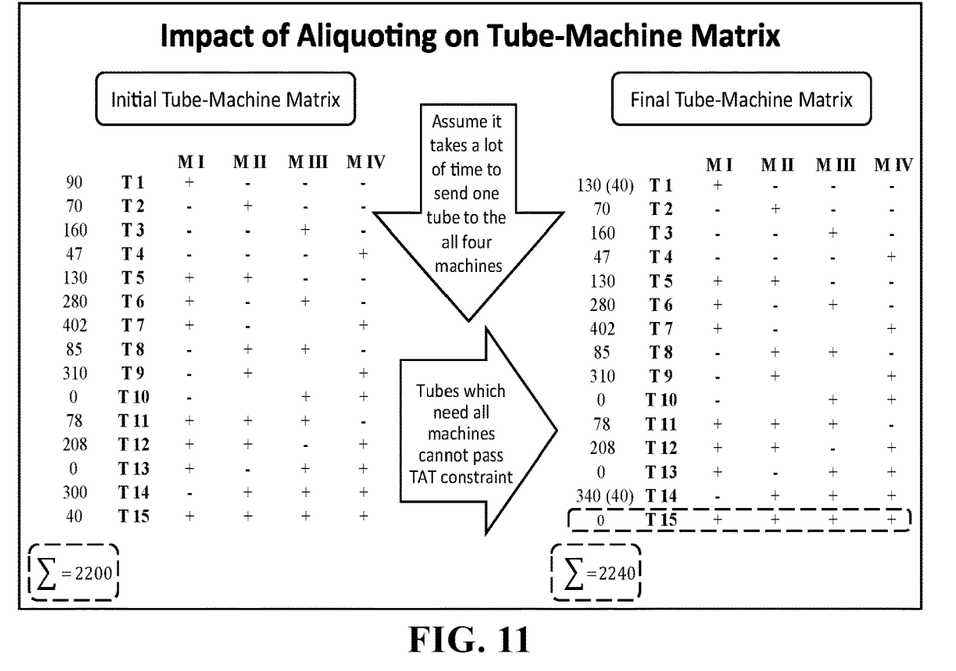
FIG. 11 illustrates an exemplary embodiment of a potential impact of aliquoting on number of tubes and a tube-machine matrix in a situation where tubes which require processing by all available machines do not pass a turn-around time constraint without aliquoting.
Figure 12:
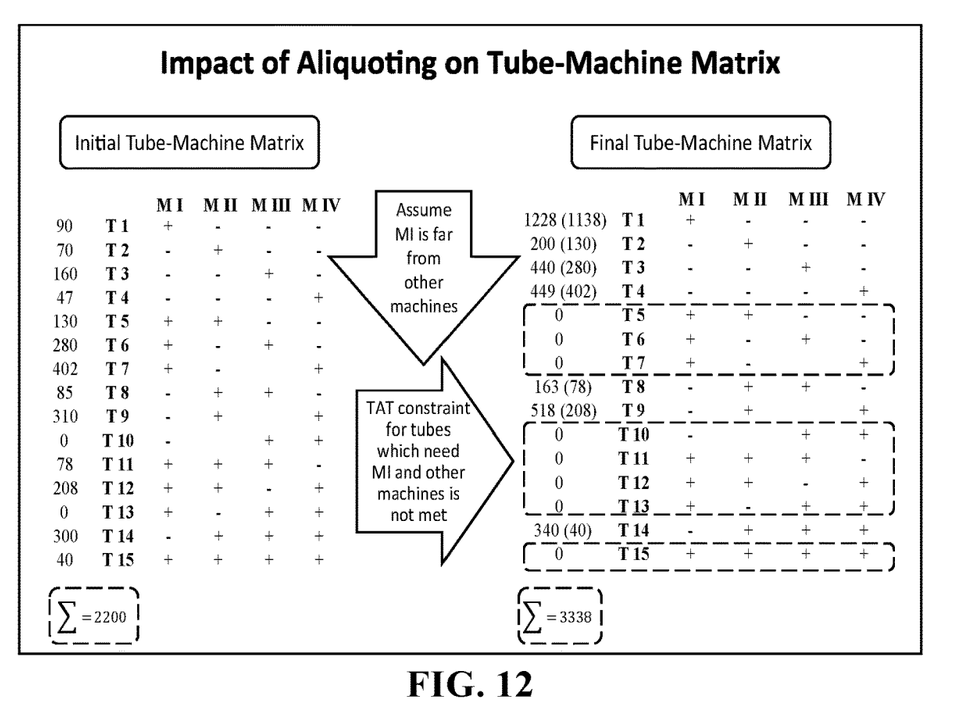
FIG. 12 illustrates an exemplary embodiment of a potential impact of aliquoting on number of tubes and a tube-machine matrix in a situation where tubes which require processing by a machine which is far from the other machines and at least one other machine do not pass a turnaround time constraint without aliquoting.
Figure 13:
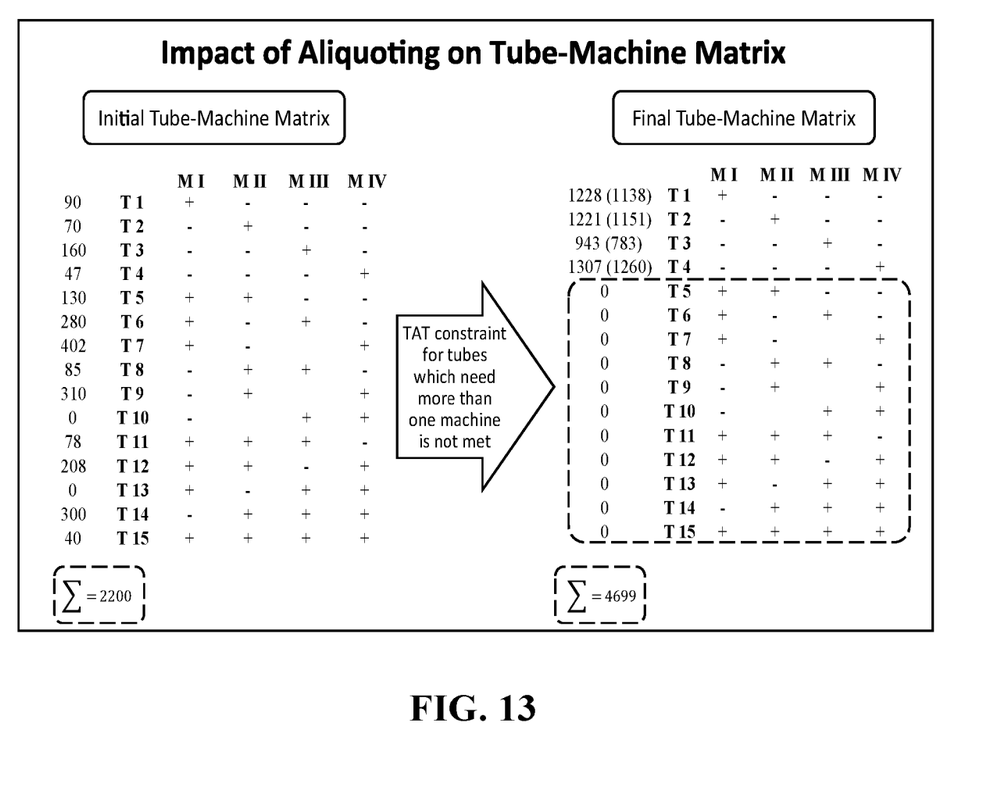
FIG. 13 illustrates an exemplary embodiment of a potential impact of aliquoting on number of tubes and a tube-machine matrix in a situation where tubes which require processing by multiple machines do not pass a turnaround time constraint without aliquoting.

Returning now to the discussion of FIG. 8, however the determination 801 is made, once it has been determined that some constraint has not been met, a potential aliquoting and test assignment may be determined 802. This could result in a revised Tube-Test Matrix, which would be used to create a new Tube-Machine Matrix and determine a new sequence and schedule for the tubes to be processed. That new sequence and schedule could be checked 801 to determine if the proposed aliquoting and test assignment would allow the relevant constraints to be met. This could then be repeated one or more times, potentially with a different aliquoting and test assignment being determined 802 each time. For example, in some embodiments, if the check 801 of FIG. 8 indicates that the constraints would not be met without aliquoting, then an initial aliquoting and test assignment could be generated using a relatively conservative aliquoting policy (i.e., one which results in a relatively small increase in the number of tubes used to hold the samples), with a more aggressive policy being used on each subsequent iteration until ultimately a schedule and sequence for the tubes which met the relevant constraints had been created. At that point, the workflow shown in FIG. 8 may be deemed complete, and the tubes could be physically aliquoted and tested in the manner which had resulted in the constraints being met. Examples of results which could be obtained from applying different types of aliquoting policies in this type of progression, and their respective impacts on the number of tubes and the Tube-Machine Matrix, are illustrated in FIGS. 11-13.

Of course, it should be understood that the above discussion is intended to be illustrative only, and that in some embodiments variations on the described dynamic aliquoting workflow may be possible and could be implemented by those of ordinary skill in the art without undue experimentation in light of this disclosure. As an example, of this type of variation, consider the step of determining an aliquoting and test assignment 802. As discussed above, in some cases, this determination may be made by applying an aliquoting policy wholesale to a set of tubes which were to be processed by a lab. However, it is also possible that, in some embodiments, this type of determination 802 could be performed in a more targeted manner, such as by only aliquoting those tubes which caused a constraint not to be met. For instance, in some embodiments, if the tubes allocated to a particular machine by the previous tube-machine matrix had caused a turnaround time requirement to be violated, then initially only those tubes could be aliquoted, rather than aliquoting all tubes to be processed. Similarly, in some embodiments, if there is a turnaround time constraint which applies to individual tubes, then aliquoting might be limited to only those tubes which violated the turnaround time constraint. In some embodiments, this type of conditional focusing could also be applied to cases where turnaround time is defined on a per-test basis, with aliquoting applied to only those tubes whose contents required a test which violated the turnaround time constraint. Indeed, in some embodiments, to avoid unnecessary aliquoting, it is possible that not all tubes which violated a constraint might be initially aliquoted. For example, when it is first determined that a constraint has been violated, only a subset of the tubes which violated the constraint (e.g., one of the tubes) could be aliquoted, with aliquoting applied to additional tubes in an iterative fashion until an acceptable aliquoting and test assignment is reached.

Additional levels of targeting may also possible in some embodiments. For example, in some embodiments it is possible that tubes which violate a turnaround time constraint could be treated as only candidates for aliquoting, and would only be aliquoted and given a new test assignment if they passed one or more additional filters. In some embodiments, in cases where candidate tubes are aliquoted only after passing through one or more exclusion filters, there may be a variety of exclusion filters which could potentially be applied. For example, in some embodiments, only candidate tubes with certain priority designations (e.g., Stat) or from certain sources (e.g., a hospital) may be aliquoted, while other candidate tubes may be excluded unless there were no candidate tubes with a priority designation or from a prioritized source to consider. In some embodiments, it may also be possible that a check may be made to ensure that aliquoting could potentially solve (or at least improve on) the problem that caused a tube to be a candidate and, if it did not, then that tube would be excluded. For example, in some embodiments, if turnaround time is defined on a per-tube basis, then a candidate tube could be excluded from aliquoting if either the statement $T_Q + T_T <= T_A + T_L$ or the statement $T_L > T_R$ is true, where $T_Q$ is the timing due to the tube's current (i.e., without aliquoting) position in the instrument queues, $T_T$ is the timing due to transporting the tube between machines, $T_A$ is the time necessary to aliquot the tube, $T_L$ is the longest time any of the aliquoted tubes would be in queue based on the current aliquoting, and $T_R$ is the turnaround time requirement for the tube. Thus, in the case where a tube with a 15 minute turnaround time requirement requires tests $T_1$ and $T_2$, and the queues for the machines which would perform tests $T_1$ and $T_2$ are, respectively, 10 and 20 minutes long, the tube could be excluded from aliquoting because, even if the tubes it was aliquoted into were put at the first available queue positions, the 15 minute turnaround time constraint would still be violated by the 20 minute wait for test $T_2$ (i.e., $T_L$ would be greater than $T_R$). In some embodiments, similar types of exclusion may also be performed for turnaround times which are defined on a per-test rather than per-tube basis (e.g., a candidate tube could be excluded from aliquoting if at least one of the tests that would need to be performed for that tube had a turnaround time constraint which could not be met based on the existing queue for the machine which would perform that test), or for characteristics other than turnaround time (e.g., a candidate tube could be excluded if there would not be enough sample to perform the necessary tests once the dead volumes of the tubes the sample would be aliquoted into were considered). Accordingly, the above discussion of excluding candidate tubes from actually being aliquoted should be understood as being illustrative only, and should not be treated as limiting.

Variations in how the step of determining an aliquoting and test assignment 802 beyond determining what tubes to aliquot may also be possible in some embodiments. To illustrate, consider the determination of the number of aliquots to create once it has been determined that a particular tube is to be aliquoted. In some embodiments, this may be done by simply determining the maximum number of aliquots and then aliquoting a sample based on that number or the number of required tests (e.g., determine the maximum number of tubes a sample could be aliquoted into considering dead volume, and then aliquot the sample into either that maximum number of tubes, or a number of tubes equal to the number of tests required for the tube prior to aliquoting, whichever is less). However, in some embodiments, other factors may be considered as well. For instance, in some embodiments, in a case where a tube is subject to a turnaround time constraint which is defined on a per-tube basis, then if that tube is to be aliquoted (e.g., if it was identified as an aliquoting candidate and satisfied any applicable exclusion criteria, in an implementation where the candidate-exclusion approach is used) it could be aliquoted into a number of tubes based on the number of machines necessary to do the tests on the tube's contents. Similarly, in some embodiments, if a tube is subject to a turnaround time constraint which is defined on a per-test basis, then if that tube is to be aliquoted it may be aliquoted to a number of tubes which is equal to the number of machines which could potentially perform the test for which a turnaround time constraint was not met. Of course, in some embodiments, other variations, such as combined approaches (e.g., using maximum number of aliquots based on dead volume as a ceiling in a case where the number of aliquots would otherwise be determined based on turnaround time constraints), may also be possible, and may be implemented without undue experimentation by those of ordinary skill in the art in light of this disclosure. Accordingly, the preceding description of variations in numbers of aliquots, like the description of variations in targeting of aliquots, should be understood as being illustrative only, and should not be treated as limiting.

It is also possible that the disclosed technology could be implemented in a manner in which whether (and/or how) to aliquot was determined dynamically, but which diverged from the basic workflow shown in FIG. 8. As an example of this, consider FIG. 15. In an embodiment following that Figure, whether to proceed with aliquoting and test assignment 802 is determined based on whether certain key performance indicators (i.e., KPIs) can be improved 1501. These KPIs may be things such as number of tubes not fulfilling turnaround time constraints, percent of tubes not fulfilling turnaround time constraints, or more high level considerations like overall lab throughput or overall sum of the delay between when tubes (or tube tests) are actually done relative to the deadlines for those tubes (or tube tests).

Figure 15:
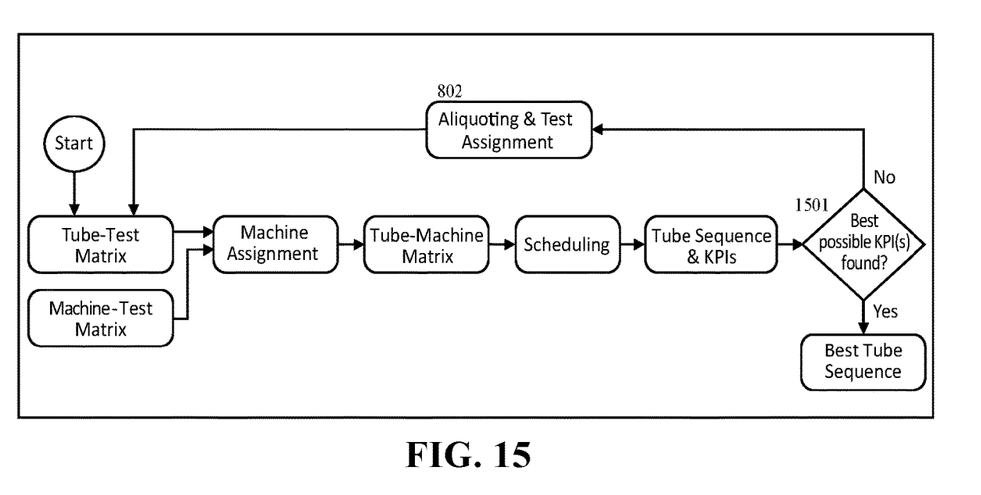
FIG. 15 illustrates an exemplary embodiment of a workflow in which aliquoting is determined dynamically based on whether key performance indicators can be improved.

In embodiments following the type of alternative workflow shown in FIG. 15, it is possible that, when a batch of tubes arrives, a computer may repeat the workflow of FIG. 2 for that batch of tubes at least once, and may continue to repeat the workflow until the KPIs stopped improving, at which point the aliquoting and test assignment which had been found to have the best impact on the KPIs may be declared optimal, and the tubes could be aliquoted and dispatched to machines based on that assignment. Of course, in some embodiments, the use of KPIs may not require new aliquoting and test assignments to be created until such time as an optimal assignment had been identified. For example, in some embodiments, KPIs may simply be compared to thresholds (e.g., no more than 5% of tubes failing to meet turnaround time requirements), and the workflow may be repeated until either the thresholds were met or the KPIs ceased improving. Similarly, in some embodiments, in cases where there are multiple acceptable solutions on the Pareto front (i.e., there are multiple solutions which meet the constraints which apply in a particular situation, but there is not one solution which strictly dominates all the others), a user may be requested to make a determination of which of the acceptable solutions would be used.

Figure 16:
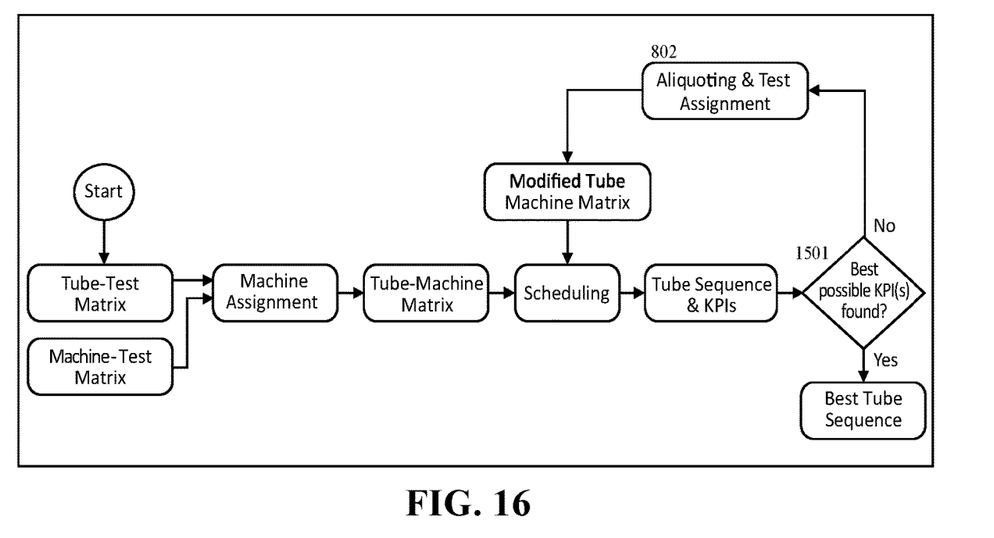
FIG. 16 illustrates an exemplary embodiment of a workflow in which aliquoting is determined dynamically with machine assignment reused for new aliquots.
Figure 17:
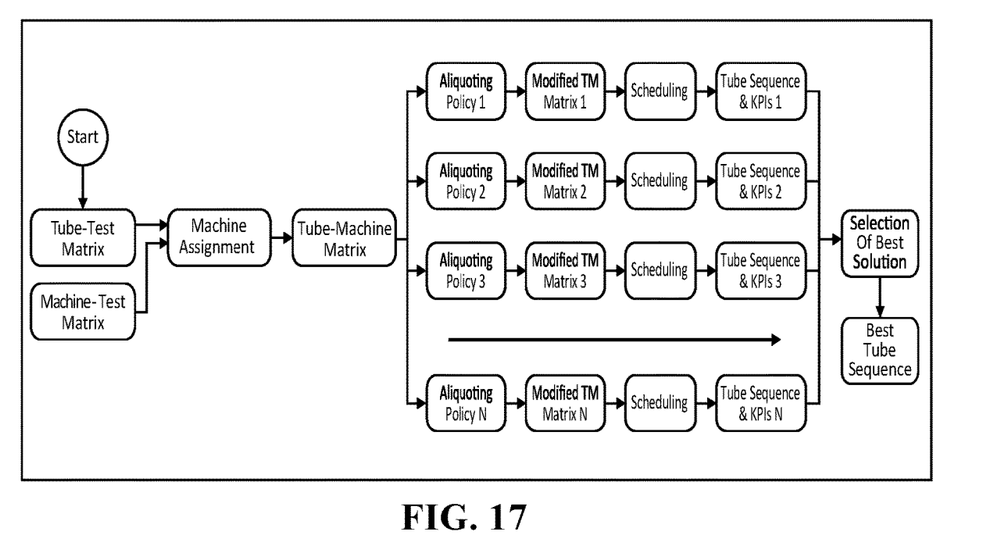
FIG. 17 illustrates an exemplary embodiment of a workflow in which aliquoting is determined dynamically and multiple aliquoting policies are applied in parallel.

Additional examples of workflows which may be used in some embodiments to dynamically determine whether and/or how aliquoting should be performed are provided in FIGS. 16 and 17. In FIG. 16, a process is shown which is similar to the processes of FIGS. 8 and 15 in that it may iteratively repeat the determination of an aliquoting and test assignment 802 until a final aliquoting and test assignment is identified. However, the process of FIG. 16 differs from those shown in FIGS. 8 and 15 in that the process of FIG. 16 may repeat a much smaller portion of the overall workflow on each iteration—reusing the machine assignments for the new aliquots rather than recomputing the tube-machine matrix for each potential aliquoting and test assignment determination 802. Of course, while FIGS. 8, 15 and 16 illustrated workflows which would iteratively determine aliquoting and test assignments 802, this iterative determination would not necessarily be present in all cases where the disclosed technology is used to implement dynamic aliquoting. An example of how the dynamic determination of aliquoting could be performed in some embodiments without iteration such as shown in FIGS. 8, 15 and 16 is provided in FIG. 17, in which multiple aliquoting policies may be applied in parallel (e.g., as different threads in a multi-threaded process, as different processes launched on a single system, etc.), and then the results of those policies may be compared with each other to determine which was most suitable for a given situation.

To further illustrate how the disclosed technology could be used to improve the handling of tubes, consider the Tube-Machine matrix set forth in table 1.

TABLE 1

Illustrative Tube-Machine Matrix

|  | Analyzer A | Analyzer B |
|---|---|---|
| Tube 1 | 2/15 | 7/30 |
| Tube 2 | 3/14 | 5/22 |
| Tube 3 | 5/20 | 4/5 |
| Tube 4 | 6/11 | 5/11 |
| Tube 5 | 3/4 | 3/23 |

Figure 7:
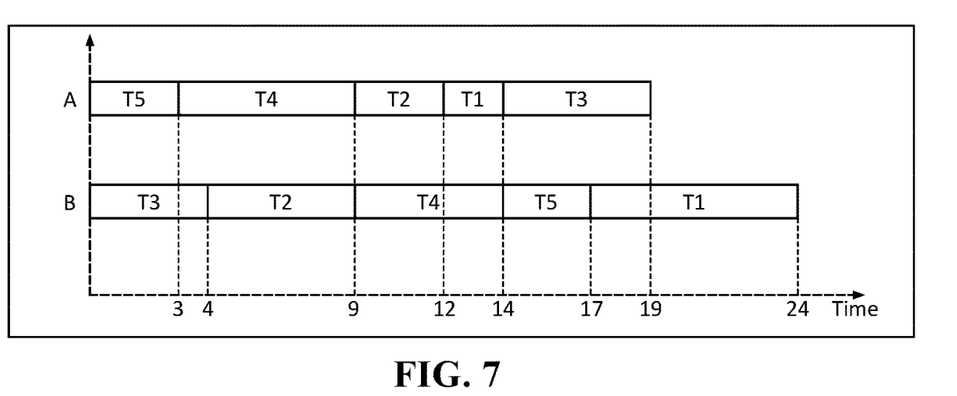
FIG. 7 providers provides a Gantt chart illustrating assignment of un-aliquoted tubes to analyzers.
Figure 10:
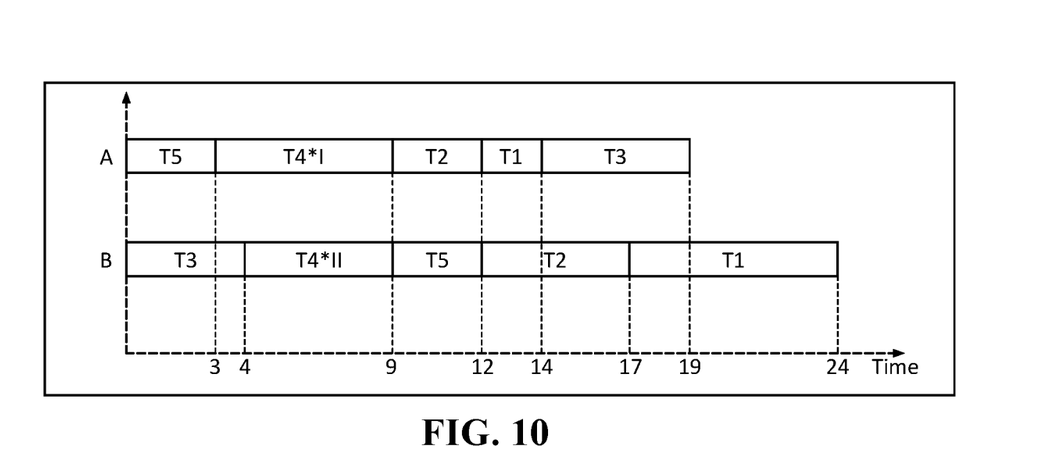
FIG. 10 provides an exemplary embodiment of a Gantt chart illustrating assignment of aliquoted tubes to analyzers.

In that table, the entries for each tube indicate both the time necessary for that tube to be processed by a particular analyzer, and the deadline for the processing of that tube by the analyzer to be complete. For example, in the situation reflected in Table 1, the operation of Analyzer A on Tube 1 takes two time units, and the due date for the processing of Tube 1 by Analyzer A is 15 time units. In scheduling, the sequence of the tubes on the analyzer would preferably be determined in a way to minimize the number of delayed operations. To achieve this objective, an earliest due date priority rule can be applied, and in the case of a tie, a shortest processing time rule may be employed to sequence tubes on the analyzers. A Gantt chart showing a schedule of un-aliquoted tubes created using this approach is provided in FIG. 7. As can be seen in the Gantt chart of FIG. 7, in the absence of aliquoting, the due date for the processing of Tube 4 on Analyzer B (i.e., 11 time units) is violated, since the processing of Tube 4 by Analyzer B would not be completed until 14 time units had elapsed. However, if Tube 4 is aliquoted and rescheduled, then this can be avoided. This can be seen in FIG. 10, which is a revised Gantt chart in which Tube 4 is replaced by tubes T4*I and T4*II, representing the tubes into which Tube 4 had been aliquoted. As shown in FIG. 10, with this aliquoting, all of the due dates for the tubes are met, and so there is no delayed operation, thereby illustrating the usefulness of the disclosed technology to comply with requirements related to processing for tubes while still avoiding the costs associated with aliquoting more tubes than are necessary.

Figure 14:
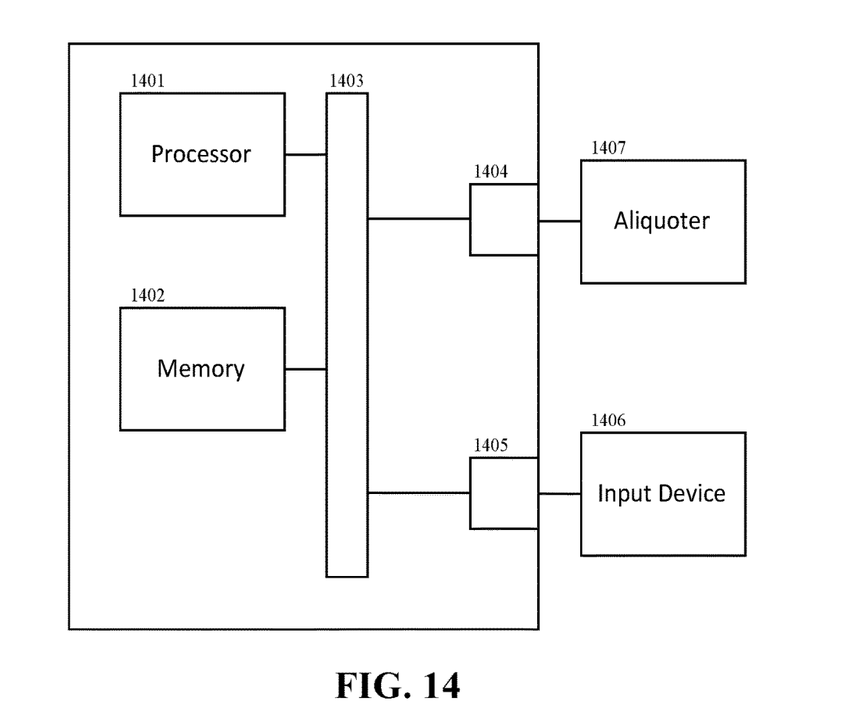
FIG. 14 illustrates an exemplary computer system which may be used in some embodiments.

Turning now to FIG. 14, that figure illustrates a computer system such as could be used to perform generation of aliquoting instructions and machine assignments in some embodiments. As shown in FIG. 14, such a computer system may include one or more processors 1401, one more computer readable memories 1402 (e.g., RAM, ROM or various other types of storage), a communication bus 1403, and one or more external device interfaces 1404 1405 (e.g., USB ports, parallel ports, TCP/IP adapter cards, etc.). In some embodiments, external device interfaces 1404 1405 may be connected to various input devices 1406 (e.g., keyboards, touch screen interfaces, etc.) and/or various laboratory machines such as aliquoters 1407. In operation, instructions for performing workflows such as described herein may be stored in the one or more computer readable memories 1402, and those instructions may be executed by a processor 1401 on input received from an external input device 1406 to generate aliquoting instructions which may be sent to an aliquoter 1407 to specify how tubes should be aliquoted. Additionally, in some embodiments, machine assignments may also be generated and sent to analytic machines which would actually process the aliquoted tubes (not shows in FIG. 14) so that in some embodiments an entire laboratory may potentially be controlled in an optimized manner as described herein.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

As used herein, the singular forms "a", "an", and "the" include plural referents unless the context clearly dictates otherwise. The invention has now been described in detail for the purposes of clarity and understanding. However, it will be appreciated that certain changes and modifications may be practiced within the scope of the appended claims.

As used herein the term "patient" refers to a human or non-human subject who is being tested, treated, monitored or the like for a medical condition, disease or the like by a custodian.

As used herein, the term "machine" refers to a device or combination of devices.

As used herein, the term "network" refers to any collection of networks using standard protocols. For example, the term includes a collection of interconnected (public and/or private) networks that are linked together by a set of standard protocols (such as TCP/IP, HTTP, etc.) to form a global, distributed network. The term is also intended to encompass variations that may be made in the future, including changes and additions to existing standard protocols or integration with other media (e.g., television, radio, etc.).

As used herein, the term "sample" refers to any biological sample, and the phrase "biological sample" is meant to cover any specimen of biological material which has been isolated from its natural environment, such as the body of an animal or a human being. It can be in solid form such as tissues, bones, ligaments, and the like. It can also be in liquid form such as blood, spinal fluid, and the like.

As used herein, the term "set" refers to a number, group, or combination of zero or more things of similar nature, design, or function.

As used herein, the term "based on" means that something is determined at least in part by the thing that it is indicated as being "based on." To indicate that something must be completely determined based on something else, it would be described as being based "exclusively" on whatever it is completely determined by.

As used herein, modifiers such as "first," "second," and so forth are simply labels used to improve readability, and are not intended to imply any temporal or substantive difference between the items they modify. For example, referring to items as a "first program" and a "second program" in the claims should not be understood to indicate that the "first program" is created first, or that the two programs would necessarily cause different things to happen when executed by a computer.

The invention claimed is:

1. A non-transitory computer readable medium storing instructions for, in response to receiving a plurality of tubes wherein each tube from the plurality of tubes contains a sample, performing a set of acts comprising:
    a) determining one or more ways to separate the samples contained in the plurality of tubes into additional tubes; and
    b) evaluating results corresponding to the one or more ways to separate the samples; and
    c) separating, using at least one aliquoter, the samples contained in the plurality of tubes based on the evaluation of results corresponding to the one or more ways to separate the samples;
    wherein determining one or more ways to separate the samples contained in a plurality of tubes into additional tubes is based on:
        i) a first matrix indicating a plurality of tests to be performed on the samples contained in the plurality of tubes, and
        ii) a second matrix indicating types of tests which laboratory instruments from a plurality of laboratory instruments are adapted to perform.

2. The non-transitory computer readable medium of claim 1, wherein the set of acts comprises:
    a) determining an initial way to separate the samples contained in the plurality of tubes into additional tubes;
    b) determining an initial result corresponding to the initial way to separate the samples contained in the plurality of tubes into additional tubes;
    c) determining whether to approve the initial way to separate the samples contained in the plurality of tubes into additional tubes based on evaluating the initial result;
    d) until a way to separate the samples contained in the plurality of tubes into additional tubes is approved, repeating the acts of:
        i) determining a new way to separate the samples contained in the plurality of tubes into additional tubes, wherein the new way to separate the samples contained in the plurality of tubes into additional tubes increases how many additional tubes the samples are separated into relative to a most recent previously determined way to separate the samples contained in the plurality of tubes into additional tubes;
        ii) determining a new result corresponding to the new way to separate the samples contained in the plurality of tubes into additional tubes; and
        iii) determining whether to approve the new way to separate the samples contained in the plurality of additional tubes based on evaluating the new result.

3. The non-transitory computer readable medium of claim 2, wherein the initial way to separate the samples contained in the plurality of tubes into additional tubes is not separating the samples contained in the plurality of tubes into additional tubes.

4. The non-transitory computer readable medium of claim 1, wherein determining one or more ways to separate the samples contained in the plurality tubes into additional tubes comprises determining a way to separate the samples contained in the plurality of tubes in parallel for each of a plurality of aliquoting policies.

5. The non-transitory computer readable medium of claim 1, wherein evaluating results corresponding to the one or more ways to separate the samples comprises determining the impact of the results on at least one key performance indicator.

6. The non-transitory computer readable medium of claim 1, wherein:
    a) evaluating results corresponding to the one or more ways to separate the samples comprises determining whether each of the evaluated results corresponds to satisfying a requirement for processing the samples; and
    b) the instructions include instructions for approving one of the one or more ways to separate the samples contained in the plurality of tubes into additional tubes even when none of the evaluated results corresponds to satisfying the requirement for processing the samples.

7. The non-transitory computer readable medium of claim 1, wherein determining one or more ways to separate the samples contained in the plurality of tubes comprises determining, for each tube from the plurality of tubes, whether one or more portions of the sample contained in that tube should be portioned into one or more additional tubes, which additional tubes are other tubes not included in the plurality of tubes containing the samples.

8. The non-transitory computer readable medium of claim 1, wherein:
a) determining the one or more ways to separate the samples comprises, for each of the one or more ways to separate the samples:
 i) determining a corresponding set of additional tubes into which to separate portions of the samples in the plurality of tubes; and
 ii) generating, as the first matrix, a corresponding tube-test matrix for that way to separate the samples, wherein the corresponding tube-test matrix indicates, for each tube from the plurality of tubes and each tube from the corresponding set of additional tubes, one or more tests to be performed using that tube's contents;
b) evaluating results corresponding to the one or more ways to separate the samples comprises, for each of the one or more ways to separate the samples:
 i) based on the corresponding tube-test matrix for that way to separate the samples, generating a corresponding machine-tube matrix for that way to separate the samples, wherein the corresponding machine-tube matrix indicates, for each tube in the plurality of tubes and each tube from the corresponding set of additional tubes, one or more laboratory instruments from a plurality of laboratory instruments to which that tube should be allocated;
 ii) generating a corresponding sequence for distributing each tube from the plurality of tubes and each tube from the corresponding set of additional tubes to the one or more laboratory instruments indicated for that tube in the corresponding machine-tube matrix for that way to separate the samples; and
 iii) determining whether the corresponding sequence for that way to separate the samples violates one or more constraints.

9. A method comprising:
a) determining a potential way of separating samples contained in a plurality of tubes into additional tubes;
b) evaluating a result of the potential way of separating samples contained in the plurality of tubes into additional tubes;
determining whether to approve the potential way of separating samples contained in the plurality of tubes into additional tubes;
d) repeating steps (a) to (c) until a determined way to separate the samples contained in the plurality of tubes into additional tubes is approved and after the determined way to separate the samples contained in the plurality of tubes into additional tubes is approved, separating the samples contained in the plurality of tubes according to the approved determined way using an aliquoter;
wherein, each time step (a) is performed, determining the potential way to separate the samples contained in a plurality of tubes into additional tubes is based on:
 i) a first matrix indicating a plurality of tests to be performed on the samples contained in the plurality of tubes, and
 ii) a second matrix indicating types of tests which laboratory instruments from a plurality of laboratory instruments are adapted to perform.

10. The method of claim 9, wherein each time steps (a) to (c) of claim 9 are performed, the potential way of separating samples contained in the plurality of tubes into additional tubes separates the samples contained in the plurality of tubes into more additional tubes than a most recent previously determined way of separating the samples.

11. A non-transitory computer readable medium storing instructions for, in response to receiving a plurality of tubes wherein each tube from the plurality of tubes contains a sample from a plurality of samples, performing a set of acts comprising:
a) determining one or more ways to separate portions of the plurality of samples from the plurality of tubes into additional tubes such that, after separation, each additional tube would contain a portion of a single sample from the plurality of samples;
b) evaluating results corresponding to the one or more ways to separate the samples; and
c) separating, using at least one aliquoter, portions of the plurality of samples from the plurality of tubes into additional tubes based on the evaluation of results corresponding to the one or more ways to separate the portions of the plurality of samples;
wherein determining one or more ways to separate the samples contained in a plurality of tubes into additional tubes is based on:
 i) a first matrix indicating a plurality of tests to be performed on the samples contained in the plurality of tubes, and
 ii) a second matrix indicating types of tests which laboratory instruments from a plurality of laboratory instruments are adapted to perform.

\* \* \* \* \*